(12) United States Patent
Knorr et al.

(10) Patent No.: US 12,357,765 B2
(45) Date of Patent: Jul. 15, 2025

(54) DWELL TIMER

(71) Applicant: Sanofi, Paris (FR)

(72) Inventors: Christopher Knorr, Bad Soden am Taunus (DE); Gregory Stern, Lexington, MA (US)

(73) Assignee: Sanofi, Paris (FR)

( * ) Notice: Subject to any disclaimer, the term of this patent is extended or adjusted under 35 U.S.C. 154(b) by 881 days.

(21) Appl. No.: 17/479,924

(22) Filed: Sep. 20, 2021

(65) Prior Publication Data

US 2022/0088314 A1 Mar. 24, 2022

Related U.S. Application Data

(60) Provisional application No. 63/082,156, filed on Sep. 23, 2020.

(30) Foreign Application Priority Data

Nov. 30, 2020 (EP) .................................. 20315468

(51) Int. Cl.
*A61M 5/315* (2006.01)
*A61M 5/24* (2006.01)
(Continued)

(52) U.S. Cl.
CPC ...... *A61M 5/3157* (2013.01); *A61M 5/31511* (2013.01); *A61M 5/24* (2013.01);
(Continued)

(58) Field of Classification Search
CPC .. A61M 5/3157; A61M 5/31511; A61M 5/24; A61M 5/31568; A61M 5/486;
(Continued)

(56) References Cited

U.S. PATENT DOCUMENTS 9,616,168 B2 4/2017 Moore
10,449,301 B2 10/2019 Plumptre et al.
(Continued)

FOREIGN PATENT DOCUMENTS

CA 3064056 1/2019
JP 2014533599 A 12/2014
(Continued)

OTHER PUBLICATIONS

International Preliminary Report on Patentability in International Appln. No. PCT/US2021/051102, mailed on Apr. 6, 2023, 9 pages.
(Continued)

*Primary Examiner* — Tasnim Mehjabin Ahmed
(74) *Attorney, Agent, or Firm* — Bond, Schoeneck & King, PLLC

(57) ABSTRACT

Electronics assemblies for an injection device. At least one of the electronics assemblies include: one or more sensors configured to capture injection information of the injection device; one or more processors configured to be communicatively coupled to the one or more sensors; and a memory communicatively coupled to the one or more processors, the memory storing instructions which, when executed by the one or more processors, cause the one or more processors to perform operations. The operations include: receiving the injection information from the one or more sensors; determining, based on the injection information, a dwell time for a user of the injection device; and causing one or more display devices to provide feedback information to the user, the feedback information indicating the determined dwell time.

20 Claims, 4 Drawing Sheets

(51) Int. Cl.
    *A61M 5/31*    (2006.01)
    *A61M 5/48*    (2006.01)

(52) U.S. Cl.
    CPC . *A61M 2005/3126* (2013.01); *A61M 5/31568* (2013.01); *A61M 5/486* (2013.01); *A61M 2205/3327* (2013.01); *A61M 2205/3561* (2013.01); *A61M 2205/50* (2013.01)

(58) Field of Classification Search
    CPC .. A61M 2005/3126; A61M 2205/3327; A61M 2205/3561; A61M 2205/50
    See application file for complete search history.

(56)    References Cited

U.S. PATENT DOCUMENTS

2014/0330206 A1*  11/2014  Moore .............. A61M 5/14216
                                                        604/152
    2016/0259913 A1*   9/2016  Yu ...................... A61M 5/31511
    2018/0154086 A1*   6/2018  Toporek ............ A61M 5/31585
    2019/0217022 A1*   7/2019  Gentz ..................... A61M 5/20

FOREIGN PATENT DOCUMENTS

JP         2018517502 A      7/2018
    WO      WO 2019/002534       1/2019
    WO      WO 2019/121617       6/2019

OTHER PUBLICATIONS

International Search Report and Written Opinion in International Appln. No. PCT/US2021/051102, dated Jan. 24, 2022, 15 pages.
Notice of Reasons for Refusal, JP Patent Application No. 2023-518354, dated May 7, 2025, pp. 1-12 (with pp. 1-6 being a translation).

* cited by examiner

DWELL TIMER

CROSS-REFERENCE TO RELATED APPLICATIONS

This application claims priority to U.S. Provisional Patent Application No. 63/082,156, filed on Sep. 23, 2020, and to European Patent Application No. 20315468.7, filed on Nov. 30, 2020, the entire contents of which are incorporated herein by reference.

TECHNICAL FIELD

This disclosure is directed to dwell timers, and more particularly, to dwell timers for injection devices.

BACKGROUND

Electronically-enabled delivery devices, such as pen-type injectors, can include dose setting means that enable the administration of medicament to a user. Electronically-enabled injection devices assist users in safely administering a medicament and can also enable transmission of treatment data to medical staff. Electronically enabled injection devices include an electronic component configured to provide continuous active sensing and connectivity properties, functions that may require an energy supply. Some uses of injection devices (for example, insulin injection devices) may require a user to wait an amount of time, known as a "dwell time," before removing the injection device from an injection site. For example, a user of an insulin injection device can be instructed to wait 5-10 seconds (i.e., "dwell time") after an injection of insulin before removing an injection needle from an injection site. This may help to avoid, for example, reflux of insulin from the injection site.

SUMMARY

Implementations of the present disclosure include mechanisms and systems that can provide a dynamic dwell timer for use in an injection device that determines a dwell time based on, for example, a speed of an injection and a size of a dosage of medicament to be administered to a user of the injection device. Information, such as instructional animations, can be presented to the user of the injection device that indicate how to perform an injection using the injection device, in which the instructions include the determined dwell time.

In an aspect, an electronics assembly for an injection device is provided. The electronics assembly includes: one or more sensors configured to capture injection information of the injection device; one or more processors configured to be communicatively coupled to the one or more sensors; and a memory communicatively coupled to the one or more processors, the memory storing instructions which, when executed by the one or more processors, cause the one or more processors to perform operations. The operations include receiving the injection information from the one or more sensors; determining, based on the injection information, a dwell time for a user of the injection device; and causing one or more display devices to provide feedback information to the user, the feedback information indicating the determined dwell time.

The injection information can include at least one of: a speed of an injection, a dosage amount of an injection, or a profile of an injection. Causing one or more display devices to provide feedback information can include causing the one or more display devices to display an animation illustrating an injection process that comprises the determined dwell time. The operations can further include receiving user information of the user, wherein determining a dwell time is further based on the user information of the user. The user information can indicate one or more of: a weight of the user, a body fat percentage of the user, a needle aversion of the user, or a drug type. Causing one or more display devices to provide feedback information can include transmitting the feedback information to a mobile device of the user which, when received by the mobile device, causes the mobile device to display one or more graphical representations representing injection instructions.

The operations can further include: determining, based on the captured injection information, a speed of injection of the user; comparing the speed of injection with an injection speed threshold; and responsive to determining that the speed of injection exceeds the injection speed threshold, activating an alert module.

In an aspect, an injection device is provided. The injection device includes a stopper. The stopper includes the aforementioned electronics assembly.

Systems in accordance with the present disclosure can include any combination of the aspects and features described herein. That is to say that systems in accordance with the present disclosure are not limited to the combinations of aspects and features specifically described herein, but also include any combination of the aspects and features provided.

These and other aspects, features, and implementations can be expressed as methods, apparatus, systems, components, program products, methods of doing business, means or steps for performing a function, and in other ways, and will become apparent from the following descriptions, including the claims.

Implementations of the present disclosure can provide one or more of the following advantages. As opposed to traditional injection devices, a dwell timer can be used to dynamically determine a dwell time for a user based on, for example, an injection speed and/or a dosage amount. For example, during/after a user uses an injection device to inject a dose of medicament at an injection site of the user, sensors can be used to determine the speed of the injection and an amount of medicament injected. Based on this information, a dwell time can be determined and presented to the user. Accordingly, when compared with traditional injection devices, injection operations of the injection device can be enhanced as the dynamic determination and presentation of a dwell time that is particular to user can, for example, reduce the amount of medicament reflux from the injection site.

The details of one or more implementations of the present disclosure are set forth in the accompanying drawings and the description below. Other features and advantages of the present disclosure will be apparent from the description and drawings, and from the claims.

DESCRIPTION OF DRAWINGS

Like reference symbols in the various drawings indicate like elements.

DETAILED DESCRIPTION

In some conventional injection devices, it is recommended to wait an amount of time after an injection, known as a "dwell time," before removing the injection device from an injection site. For example, a user of an insulin injection device can be instructed to wait 5-10 seconds (i.e., "dwell time") after an injection of insulin before removing an injection needle from an injection site. This may help to avoid, for example, reflux of insulin from the injection site.

However, these recommended dwell times are typically based on general assumptions and may not account for factors that can further reduce reflux of medicament from an injection site. For example, to determine an optimal dwell time (i.e., a dwell time that minimize reflux of medicament while minimizing the time of dwell) factors such as the speed of the injection, the profile of the injection, the dosage amount of the injection, the weight of the user, and the body fat percentage of the user, among others, can be used. Furthermore, these recommended dwell times may not account for a user's aversion to needles and/or pain, which may cause the user to disregard recommended dwell times.

The systems and methods described in this disclosure can be used to remedy the aforementioned disadvantages. In some implementations, the systems and methods described in this disclosure uses one or more sensors to determine a dwell time for a user based on, the speed of an injection, a profile of an injection, a dosage amount of an injection, or a combination of these, among others. In some implementations, the systems and methods of this disclosure determine a dwell time for a user based on a weight of the user, a body fat percentage of a user, or a combination of these, among others. In some implementations, the systems and methods described in this disclosure determines, based on a user's affinity of needles (for example, a desire to minimize dwell time), a recommended injection speed, injection profile, or a combination of these.

Figure 1:
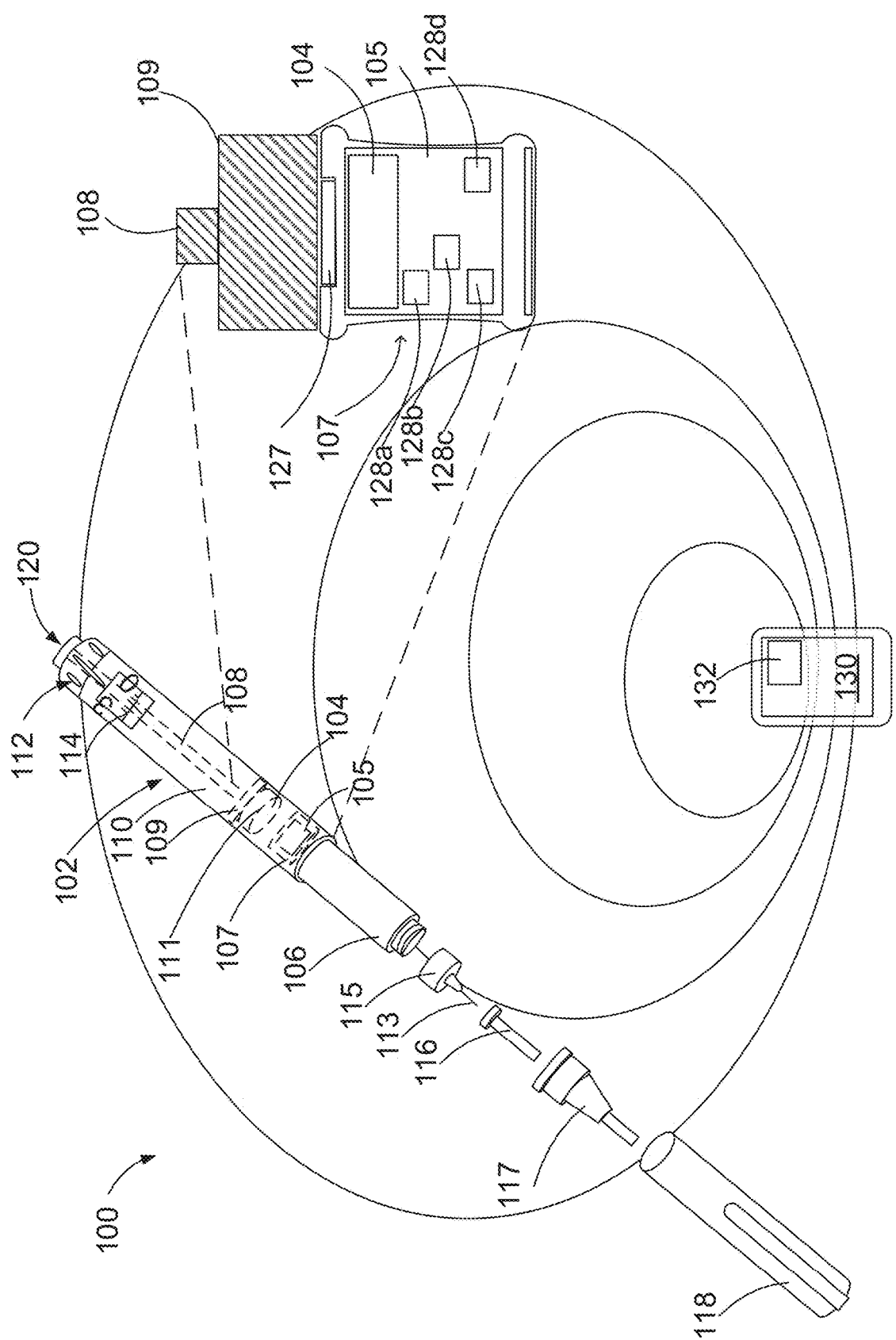
FIG. 1 is an exploded view of a medicament injection system, according to one or more implementations of the present disclosure.

FIG. 1 illustrates an exploded view of an example medicament injection system 100, according to an embodiment of the present disclosure. The medicament injection system 100 can be configured to assist a user in injecting a fluid (for example, a medicament) and facilitate sharing of medical data. The example medicament injection system 100 includes an injection device 102 and an external device 130. The injection device 102 can be a pre-filled, disposable injection pen or the injection device 102 can be a reusable injection pen with replaceable medicament reservoirs 106. In some implementations, the injection device 102 is capable of communicating with the external device 130. In some implementations, the injection device 102 is capable of transmitting to the external device 130 operational data (for example, data related to time of start of usage of injection device 102, feedback information determined by components of the injection device 102, and so forth) and corresponding treatment data (for example, amount of medicament dispensed, elapsed time for medicament to be dispensed by the injection device 102). In some implementations, the injection device 102 is associated with an identifier that is used by the external device 130 to uniquely identify the injection device 102.

The injection device 102 includes a housing 110 and a needle assembly 115. The housing 110 includes an energy source 104, an electronics assembly 105, a medicament reservoir 106, a stopper 107, a plunger rod 108, a plunger head 109, a priming component (for example, dosage knob) 112, a dosage window 114, and an injection button 120. The housing 110 can be molded from a medical grade plastic material such as a liquid crystal polymer. In some implementations, the stopper 107 includes at least one of the electronics assembly 105 or the energy source 104.

The medicament reservoir 106 is configured to contain a fluid medicament. The medicament reservoir 106 can be a conventional, generally cylindrical, disposable container like a cartridge or a syringe used to package prepared fluids such as medicaments, anesthetics and the like. In some implementations, the medicament reservoir 106 is provided with a pair of ends, with one end having a pierceable membrane, which receives an inward end of needle 113 in sealing engagement. A dose of the contained medicament can be ejected from the injection device 102 by turning the dosage knob 112. The selected dose is displayed via dosage window 114, for instance in multiples of so-called International Units (IU), where one IU is the biological equivalent of about 45.5 micrograms of pure crystalline medicament (for example, 1/22 mg). An example of a selected dose displayed in dosage window 114 may for instance be 30 IUs, as shown in FIG. 1. In some implementations, the selected dose is displayed differently, for instance by an electronic display (for example, the dosage window 114 may take the form of an electronic display). Turning the dosage knob 112 can cause a mechanical click sound to provide acoustical feedback to a user. The numbers displayed in dosage window 114 can be printed on a sleeve that is contained in housing 110 and mechanically interacts with a plunger head 109 that is fixed at the end of the plunger rod 108 and pushes the stopper 107 of the medicament reservoir 106. In some implementations, the dosage window 114 includes an alert module (for example, an electronic display that can flash red lights), which can be activated by the electronics assembly 105, as described later.

The plunger head 109 (for example, a back end of the plunger rod 108) is operable to expel a portion of the fluid by displacing the stopper 107 within the medicament reservoir 106, such that a position of the stopper 107 is associated with an amount of the fluid within the injection device 102. The plunger rod 108 is mounted to the plunger head 109. However, in some implementations, the plunger rod 108 and the plunger head 109 are separate components. In some implementations, the plunger head 109 is mounted to the stopper 107.

The stopper 107 is a flexible stopper, such as a rubber stopper. The stopper 107 can include a rigid member surrounding the stopper 107. In some implementations, the stopper 107 is a rigid stopper with a sealing component. The stopper 107 can have an outwardly projecting rim matching the geometry and dimensions 111 of the energy source 104. In some implementations where the stopper 107 is a flexible stopper, the stopper 107 is capable of transitioning between a first size and a second size in response to a change in pressure acting on the stopper 107. For example, the stopper 107 can be in a contracted state (first size) when the stopper is sealed in a vacuum condition, and then transition to an expanded state (second size) when the vacuum seal is broken and the stopper 107 experiences normal atmospheric pressure conditions. The stopper 107 can be of a sufficient length so that the stopper 107 is not ripped or twisted when being engaged by the plunger head 109. In some implementations, the stopper 107 includes the energy source 104 and the electronics assembly 105, among other components. Consequently, the stopper 107 can include sufficient volume to house these components.

The electronics assembly 105 includes one or more sensors 128b. In some implementations, the one or more sensors 128b include at least one of a force sensor, a pressure sensor, a speed sensor, or a position sensor. In some implementations, the energy source 104 provides minimal power for allowing the one or more sensors 128b enough power to operate sufficiently. In some implementations, the one or more sensors 128b have a separate power source, or have their own power source. As will be discussed later in more detail with reference to FIG. 2, in some implementations, the electronics assembly 105 is capable of detecting an amount of medicament expelled from the injection device 102 based on signals generated by the one or more sensors 128b. The electronics assembly 105 also includes an electromechanical switch 127. The electromechanical switch 127 is an electrical switch, such as a piezo switch, that is capable of generating an electrical charge based on a force being applied to the switch 127 (that is, upon activation of the switch 127). In some implementations, the electromechanical switch 127 is located on an inner surface of the stopper 107. In other implementations, the electromechanical switch 127 is located on an external surface of the stopper 107.

The energy source 104 can be a disposable or rechargeable battery, such as a 1.5V-5 V silver-oxide or lithium battery (for example, SR626, SR516, SR416) or a super capacitor. In some implementations, the energy source 104 includes a plurality of batteries (for example, two 1.5V batteries). The energy source 104 is communicatively coupled to the electromechanical switch 127.

The electronics assembly 105 includes one or more electronic components configured to perform and/or assist with one or more functions of the injection device 102 (for example, the ejection of the medicament) upon activation of the energy source 104. For example, the electronics assembly 105 can include one or more processors 128a, one or more sensors 128b, an antenna 128c, and a motor 128d. In some implementations, the motor 128d is configured to advance in micro-step increments to dispense a particular amount of medicament. In some implementations, the one or more sensors 128b are configured to provide, to the one or more processors 128a, a signal (for example, a voltage), which is proportional to the amount of medicament dispensed or amount of medicament remaining in the medicament reservoir 106.

In some implementations, the one or more processors 128a include a microprocessor. In some implementations, the microprocessor is a microcontroller, for example, a combination of microprocessor components and other components formed in a single package. The microprocessor can be an arithmetic and/or a logic unit array. The one or more processors 128a are capable of processing one or more signals received from the other electronic components of the electronics assembly 105 (such as the sensors 128b) and transmitting a signal to the antenna 128c. For example, the one or more processors 128a can be configured to execute operations on received data to generate output data. In some implementations, the one or more processors 128a are capable of determining the amount of the fluid within the injection device 102 based at least in part on an electrical signal, and transmitting the data including information related to the amount of the fluid to the antenna 128c, which can then transmit it to the external device 130. In some implementations, the electronics assembly 105 can be communicatively coupled with the dosage window (for example, when the dosage window 114 comprises an electronic display). In such implementations, the electronics assembly 105 can cause the dosage window 114 to display information, such as feedback information.

The antenna 128c can be a bluetooth or near-field communication (NFC) antenna. The antenna 128c is capable of transmitting signals to the one or more processors 128a and to the external device 130. For example, the signals transmitted by the antenna 128c can include the amount of the fluid in the medicament reservoir 106, values measured by each of the one or more sensors 128b, and the identifier of the injection device 102. A communication field 134 can be a bluetooth field or an NFC field, generated by the external device 130. The external device 130 can include a bluetooth or a RF module, a transmitter, a receiver, and an external processor 132. The external processor 132 can be configured to process the data transmitted by the injection device 102. The external device 130 can be configured to display (for example, through a graphical user interface) the data received from the injection device 102 and processed by the external processor 132.

The needle assembly 115 includes a needle 113 capable of being affixed to the housing 110. The needle 113 can be covered by an inner needle cap 116 and an outer needle cap 117, which in turn can be covered by a cap 118. When the needle 113 is inserted into a skin portion of a patient, and then injection button 120 is pushed, the medicament dose displayed in dosage window 114 is ejected from injection device 102. When the needle 113 of injection device 102 remains for a certain time in the skin portion after the injection button 120 is pushed, a high percentage (for example, more than 90%) of the dose can be injected into the patient's body. Ejection of the medicament dose can generate a mechanical click sound, which can be different from the sounds produced when using dosage knob 112.

The injection device 102 can be used for several injection processes until either the medicament reservoir 106 is empty or the expiration date of the injection device 102 (for example, 28 days after the first use) is reached. Before using the injection device 102 for the first time, it may be necessary to perform a priming operation to couple the energy source 104 to the electric component and/or to remove air from medicament reservoir 106 and needle 113. For instance, the priming operation can include selecting two units of medicament and pressing the injection button 120 while holding injection device 102 with the needle 113 upwards.

In some implementations, the electronic components of the electronics assembly 105 are integrated within the housing 110 at a single location, or at multiple locations (for example, within or attached to a plunger rod 108, and a cavity in the plunger head 109). In some implementations, one or more components of the electronics assembly 105 are included within the stopper 107. In some implementations, one or more components of the electronics assembly 105 are included within the plunger head 109.

In some implementations, at least one of the location of the energy source 104, or the location of one or more electronic components of the electronics assembly 105, are selected independent from the coupling between the electronics assembly 105 and the energy source 104. In some implementations, one or more characteristics of one or more electronic components of the electronics assembly 105, or one or more characteristics of the energy source 104, are selected to couple or uncouple the electronics assembly 105 from the energy source 104.

In some implementations, the housing 110 of the injection device 102 is configured to be separated or broken in multiple segments to provide a user access to the energy source 104, to enable separate disposal of the energy source 104. In some implementations, the medicament reservoir 106 to be assembled with the injection device 102 is manufactured with an inserted stopper 107, is filled with the fluid medicament, and is closed with a crimp seal.

In some implementations, during the manufacturing and storage of the medicament reservoir 106 and prior to assembly with the injection device 102, the energy source 104 is not activated. By keeping the energy source 104 deactivated, excessive idle drainage of energy may not occur during manufacturing and potential long storage of the medicament reservoir 106. In a subsequent step of using the injection device 104, the energy source 104 of the injection device 102 is activated by the electromechanical switch 127 to power the electronics assembly 105. In some implementations, the energy source 104 is connected to the electronics assembly 105 to enable controls of functionality of the injection device 102 upon receipt of an activation signal. In some implementations, the energy source 104 is temporarily activated during assembly to confirm proper operation of the injection device 102 and the electronics assembly 105. Connection to the energy source 104 as manufacturing step allows to wake-up the electronics assembly 105 and to generate feedback signals that confirm proper system functionality. After performing such in-process controls, the energy source 104 may be disconnected again, or the electronics assembly 105 may be set in a sleep-mode through appropriate software features that reduce energy consumption until the energy source 104 is activated.

Figure 2:
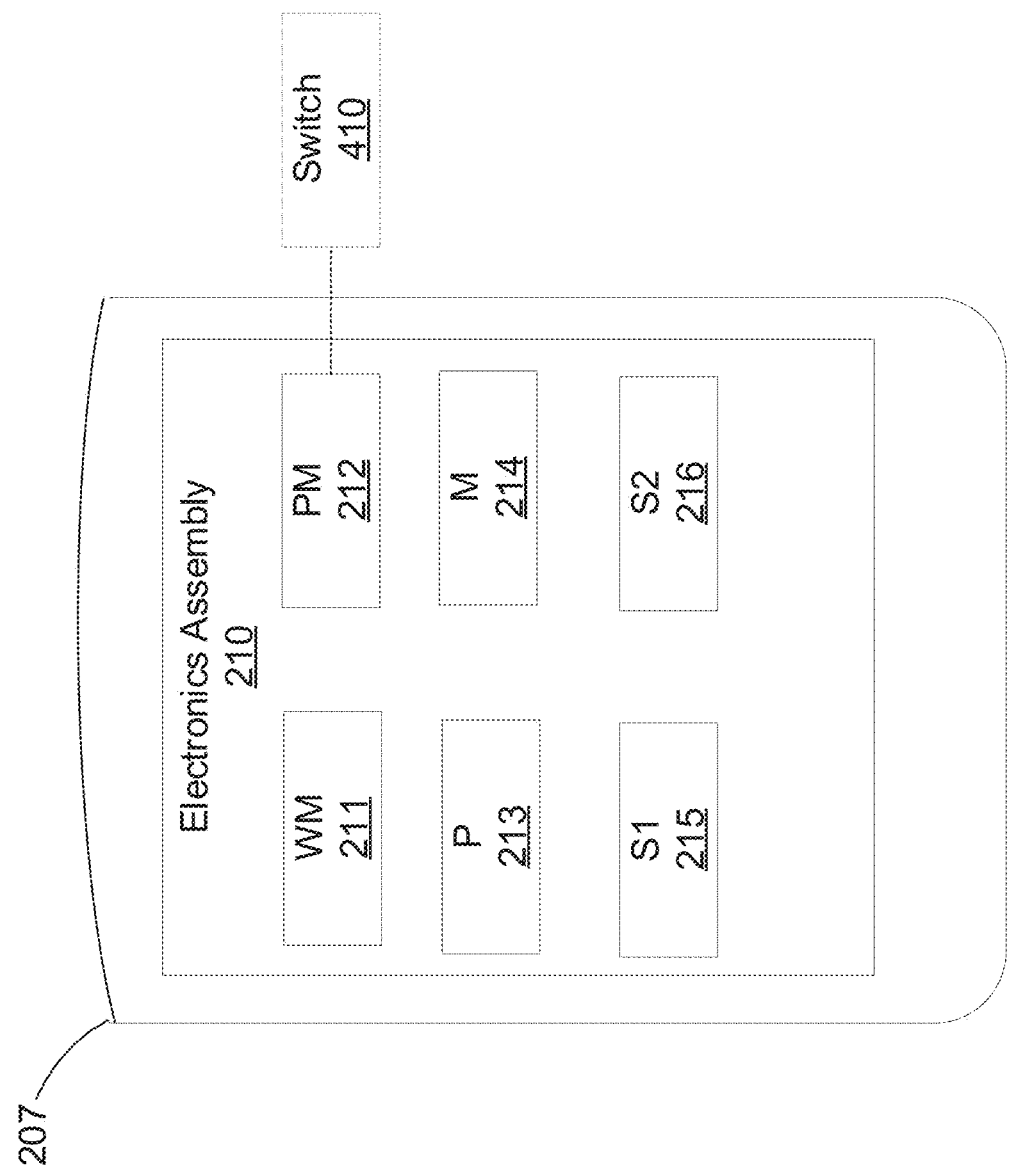
FIG. 2 illustrates a stopper having an electronics assembly, according to one or more implementations of the present disclosure.

FIG. 2 illustrates a stopper 207 having an electronics assembly 210, according to an embodiment of the present disclosure. In some implementations, the stopper 107 discussed previously with reference to FIG. 1 is substantially similar to the stopper 207 shown in FIG. 2. The stopper 207 includes an expandable rubber material (for example, neoprene, M18, silicone rubber, etc.). The stopper 207 includes an electronics assembly 210. In some implementations, the electronics assembly 105 discussed previously with reference to FIG. 1 is substantially similar to the electronics assembly 210 shown in FIG. 2.

The electronics assembly 210 includes a pressure or force sensor 215, a position sensor 216, a processor 213, a memory 214, a wireless module 211, and a power module 211. The pressure or force sensor 215, and the position sensor 216 are arranged in the electronics assembly 210 such that, when the electronics assembly 210 is disposed in the stopper 207, the position sensor 216 is able to send and receive a sensing signal into the inner volume of the medicament reservoir 106 or otherwise detect the position of the stopper 207 or the plunger rod 108 (or plunger head 109), and the pressure or force sensor 215 is able to measure the force applied to the stopper 207 (or the electronics assembly 210) via the plunger head 109 of the injection device 102 or otherwise to detect the pressure in the plunger rod 108. The processor 213 is operably coupled to all of the elements of the electronics assembly 210 and controls activation of the pressure sensor 215, the position sensor 216, and the wireless module 211. The memory 214 stores instructions for use by the processor 213 in operating the components of the electronics assembly 210.

While FIG. 2 illustrates the electronics assembly 210 in the stopper 207 with the pressure or force sensor 215 integral to the electronics assembly 210, in other instances the pressure or force sensor 215 is external to the electronics assembly 210 (for example, located at the point of contact by the plunger rod 108, attached to the plunger rod 108 itself, etc.). While FIG. 2 shows the electronics assembly 210 inside the stopper 207, in some implementations the electronics assembly 210, with or without an internal pressure or force sensor 215, is located elsewhere in the injection device 102 such that it is capable of receiving a signal from the pressure or force sensor 215.

The wireless module 211 is configured to communicate with an external electronic device in order to communicate information from the electronics assembly 210. In some implementations, the wireless module 211 includes an antenna (or transceiver), such as the antenna 128*c* discussed previously with reference to FIG. 1. The power module 212 includes an energy source, such as the energy source 104 discussed previously with reference to FIG. 1, and is configured to provide electric power to the all of the components of the electronics assembly 210. The power module 212 also includes an electromechanical switch 410, which can be substantially similar to the electromechanical switch 127 discussed earlier with reference to FIG. 1. The electromechanical switch is configured to activate the power module 212 upon the application of a force on the electromechanical switch 410. For example, when a force is applied to the electromechanical switch 410, the electromechanical switch 410 can become activated to generate and transmit an electric signal, which can be received by the power module 212. When the power module 212 receives the electric signal, it becomes activated. Upon activation, the power module 212 provides electric power to the components of the electronics assembly 210. In some implementations, the electronics assembly 210 includes a capacitive device, which includes capacitive circuitry configured to receive power wirelessly from, for example, a smartphone via a nearfield communication protocol (NFC) signal, or by a typical wireless charging device with other means of inductive loading, in order to provide energy to the power module 210.

While FIG. 2 illustrates the electronics assembly 210 including a wireless module 211, in some instances there is no wireless connectivity, and injection device 102 or the electronics assembly 210 itself contains an alert mechanism configured to visually or audibly alert a user or provide certain information to a user. For example, a representative alert mechanism could be a display or series of LED lights arranged to illuminate a different color to a user based on the sensed pressure or force signal and a determined indication of the quality of a drug delivery operation. For instances, a blue light could indicate that the device is ready to use, an orange light could be illuminated while the drug delivery device is conducting the drug delivery operation, and then a green or red light could come on at the sensed completion of the drug delivery operation to indicate a successful or failed delivery operation, respectively. In other instances, the alert mechanism could produce different sounds or beeps to convey the same or different information as the visual alert mechanism.

In some implementations, the electronics assembly 210, through the use of the sensors 215,216, is capable of detecting an amount of medicament expelled from the injection device 102. For example, through the use of the position sensor 216, the electronics assembly 210 can detect the location of the stopper 207 in the medicament reservoir 106 (or a change of location), and based on this information, determine an amount of medicament expelled. Additionally, or alternatively, the electronics assembly 210 can use the force (or pressure) sensor 215 to determine how much force is being applied to the stopper 207 (or an amount of time the force is being applied to the stopper 207) to determine an amount of medicament expelled.

The electronics assembly 210, through the user of the sensors 215,216 can capture injection information of the injection device 102. In some implementations, the electronics assembly 210, through the use of the sensors 215, 216, is capable of detecting a speed of an injection of medicament from the injection device 102. For example, through the use of the position sensor 216, the electronics assembly can determine a rate of change in location of the stopper 207 in the medicament reservoir 105, and based on this information, determine a speed at which medicament is being injected from the injection device 102. Additionally, or alternatively, the electronics assembly 210 can use the force (or pressure) sensor 215 to determine how much force is being applied to the stopper 207 (and/or an amount of time the force is being applied to the stopper 207) to determine the speed at which medicament is being expelled from the injection device 102.

In some implementations, the electronics assembly 210 is capable of receiving user information, such as a user's body weight, body fat percentage, aversion to needles, and so forth. For example, a user can use the external device 130 to input such user information, and the external device 130 can transmit the user information to the electronics assembly 210.

Based on the aforementioned injection information, the processor 213 is capable of determining a dwell time for a user. Once the dwell time is determined, the electronics assembly 210 can cause one or more display device to provide feedback information to the user that indicated the determined dwell time. In some implementations, providing feedback information includes causing an electronic display of the injection device 102 (for example, when the dosage window 114 includes an electronic display or when other components of the injection device 102 include an electronic display) to display one or more graphical representations indicating the dwell time (for example, "RECOMMENDED DWELL TIME=11.2 SECONDS"). In some implementations, providing feedback information includes transmitting the feedback information to the external device 130 in which, when received by the external device 130, causes the external device 130 to display one or more graphical representations indicating the dwell time. In some implementations, the one or more graphical representations include animations, still images, or both, that provide instructions on how to use the injection device 102, in which the instructions instruct the user to utilize the recommended dwell time when injecting the medicament at an injection site.

In some implementations, the electronics assembly 210 is configured to determine a recommended injection speed for the user. For example, based on received user information that indicates the user is more sensitive to needle pain than an average user, along with one or more of the user's body weight or body fat percentage, the processor 213 can determine a desired injection speed that will minimize dwell time.

In some implementations, the electronics assembly 210 is configured to compare the captured injection speed with an injection speed threshold. If the captured injection speed exceeds the injection speed threshold, the electronics assembly 210 can activate an alert module. For example, if the captured injection speed exceeds the injection speed threshold, the electronics assembly 210 can cause the dosage window 114 to flash (for example, when the dosage window 114 includes an electronic display) and/or transmit alert data to the external device 130 that, when received by the external device 130, causes the external device to alert the user (for example, vibrate, produce an audible sounds, display an alert, and so forth).

In some implementations, the switch 410 can be activated to power the electronics assembly 210 by a user performing a function that the user already performs during the operation of the injection device 102 for dispensing a medicament (for example, operating the plunger rod 108 or opening a sealed package that includes the injection device 102), such that additional steps (for example, manually pushing an additional push-button) may not be necessary to power the electronics assembly 210.

Figure 3:
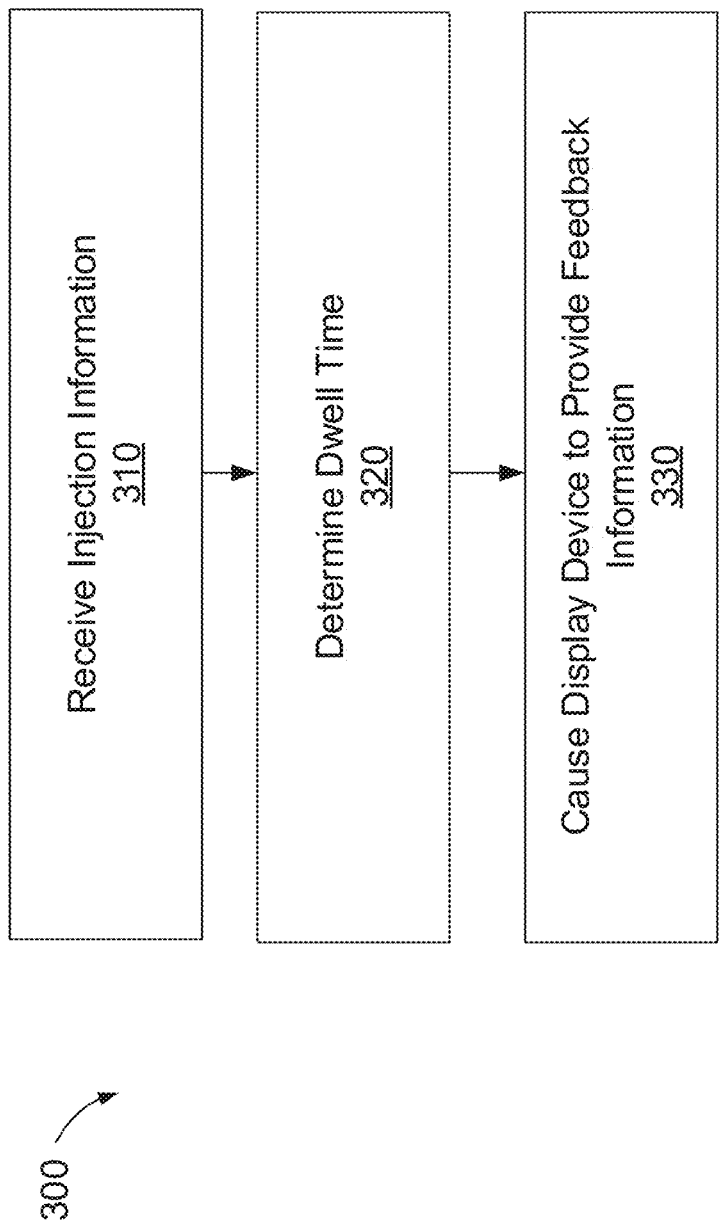
FIG. 3 is a flowchart illustrating a method for determining a dwell time, according to one or more implementations of the present disclosure.

FIG. 3 is a flowchart illustrating a method 300 for determining a dwell time, according to one or more implementations of the present disclosure. For illustrative purposes, the method 300 is described as being performed by the electronics assembly 210 discussed previously with reference to FIG. 2. The method 300 includes receiving injection information (block 310), determining a dwell time (block 320), and causing a display device to provide feedback information (block 330).

At block 310, the processor 213 receives injection information from the sensors 215,216. As indicated previously, the electronics assembly 210, through the use of the sensors 215, 216, can capture injection information of the injection device 102. For example, through the use of the position sensor 216, the electronics assembly 210 can determine a rate of change in location of the stopper 207 in the medicament reservoir 105, and based on this information, determine a speed at which medicament is being injected from the injection device 102. As another example, the electronics assembly 210 can use the force (or pressure) sensor 215 to determine how much force (or pressure) is being applied to the stopper 207 (and/or an amount of time the force or pressure is being applied to the stopper 207) to determine the speed at which medicament is being expelled from the injection device 102. Additionally, or alternatively, through the use of the position sensor 216, the electronics assembly 210 can detect the location of the stopper 207 in the medicament reservoir 106 (or a change of location), and based on this information, determine an amount of medicament expelled. As another example, the electronics assembly 210 can use the force (or pressure) sensor 215 to determine how much force is being applied to the stopper 207 (or an amount of time the force is being applied to the stopper 207) to determine an amount of medicament expelled.

In some implementations, the electronics assembly 210 is capable of receiving user information, such as a user's body weight, body fat percentage, aversion to needles, and so forth. For example, a user can use the external device 130 to input such user information, and the external device 130 can transmit the user information to the electronics assembly 210.

At block 320, the processor 213, based on the received injection information, determines a dwell time for a user. As indicated previously, the electronics assembly 210 is capable of receiving user information, such as a user's body weight, body fat percentage, aversion to needles, and so forth. The determined dwell time can be further based on the received user information.

At block 330, once the dwell time is determined, the electronics assembly 210 causes one or more display device to provide feedback information to the user that indicated the determined dwell time. In some implementations, providing feedback information includes causing an electronic display of the injection device 102 (for example, when the dosage window 114 includes an electronic display or when other components of the injection device 102 include an electronic display) to display one or more graphical representations indicating the dwell time (for example, "RECOMMENDED DWELL TIME=11.2 SECONDS"). In some implementations, providing feedback information includes transmitting the feedback information to the external device 130 in which, when received by the external device 130, causes the external device 130 to display one or more graphical representations indicating the dwell time. In some implementations, the one or more graphical representations include animations, still images, or both, that provide instructions on how to use the injection device 102, in which the instructions instruct the user to utilize the recommended dwell time when injecting the medicament at an injection site.

Figure 4:
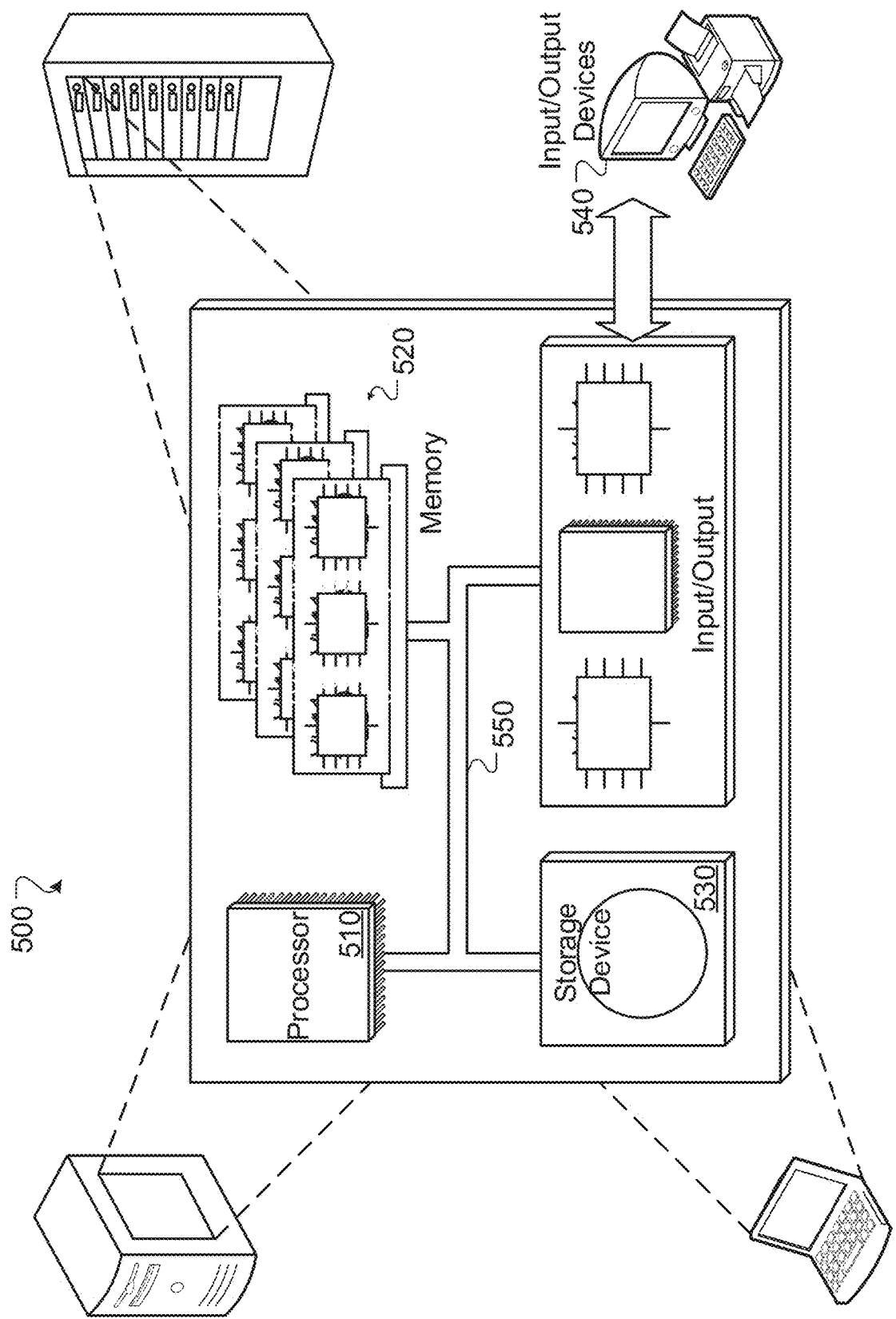
FIG. 4 is a schematic illustration of example computer systems that can be used to execute implementations of the present disclosure.

FIG. 4 shows a schematic diagram of an example computing system 500. The system 500 can be used for the operations described in association with the implementations described herein. For example, the system 500 may be included in any or all of the server components discussed herein. The system 500 includes a processor 510, a memory 520, a storage device 530, and an input/output device 540. Each of the components 510, 520, 530, and 540 are interconnected using a system bus 550. The processor 510 is capable of processing instructions for execution within the system 500. In one implementation, the processor 510 is a single-threaded processor. In another implementation, the processor 510 is a multi-threaded processor. The processor 510 is capable of processing instructions stored in the memory 520 or on the storage device 530 to display graphical information for a user interface on the input/output device 540.

The memory 520 stores information within the system 500. In one implementation, the memory 520 is a computer-readable medium. In one implementation, the memory 520 is a volatile memory unit. In another implementation, the memory 520 is a non-volatile memory unit. The storage device 530 is capable of providing mass storage for the system 500. In one implementation, the storage device 530 is a computer-readable medium. In various different implementations, the storage device 530 may be a floppy disk device, a hard disk device, an optical disk device, or a tape device. The input/output device 540 provides input/output operations for the system 500. In one implementation, the input/output device 540 includes a keyboard and/or pointing device. In another implementation, the input/output device 540 includes a display unit for displaying graphical user interfaces that enable a user to access data related to an item that is collected, stored and queried as described with reference to FIGS. 1-3.

The features described can be implemented in digital electronic circuitry, or in computer hardware, firmware, software, or in combinations of them. The apparatus can be implemented in a computer program product tangibly embodied in an information carrier, for example, in a machine-readable storage device, for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory, a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, for example, a LAN, a WAN, and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other implementations are within the scope of the following claims.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (for example, hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "injection device" shall encompass any type of device or system configured to dispense a volume of a drug into a human or animal body. The volume can typically range from about 0.5 ml to about 10 ml. Without limitation, the drug delivery device may include a syringe, needle safety system, pen injector, auto injector, large-volume device (LVD), pump, perfusion system, or other device configured for subcutaneous, intramuscular, or intravascular delivery of the drug. Such devices often include a needle, wherein the needle can include a small gauge needle (for example, greater than about 24 gauge, and including 27, 29, or 31 gauge).

In combination with a specific drug, the presently described devices may also be customized in order to operate within required parameters. For example, within a certain time period (for example, about 3 to about 20 seconds for injectors, and about 5 minutes to about 60 minutes for an LVD), with a low or minimal level of discomfort, or within certain conditions related to human factors, shelf-life, expiry, biocompatibility, environmental considerations, etc. Such variations can arise due to various factors, such as a drug ranging in viscosity from about 3 cP to about 50 cP.

The drug or medicament may be contained in a primary package or "drug container" adapted for use with a drug delivery device. The drug container may be, for example, a cartridge, syringe, reservoir, or other vessel configured to provide a suitable chamber for storage (for example, short- or long-term storage) of one or more pharmaceutically active compounds. For example, in some instances, the chamber may be designed to store a drug for at least one day (for example, 1 to at least 30 days). In some instances, the chamber may be designed to store a drug for about 1 month to about 2 years. Storage may occur at room temperature (for example, about 20° C.), or refrigerated temperatures (for example, from about −3° C. to about 3° C.). In some instances, the drug container may be or may include a dual-chamber cartridge configured to store two or more components of a drug formulation (for example, a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (for example, by way of a conduit between the two chambers) and allow mixing of the two components when desired by a user prior to dispensing. Alternatively, or in addition, the two chambers may be configured to allow mixing as the components are being dispensed into the human or animal body.

The injection devices and drugs described herein can be used for the treatment and/or prophylaxis of many different types of disorders. Exemplary disorders include, for example, diabetes mellitus or complications associated with diabetes mellitus such as diabetic retinopathy and thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, for example, human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (for example, therapeutic effectiveness).

Exemplary insulin analogues are Gly(A21), Arg(B31), Arg(B32) human insulin (insulin glargine); Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin; B29-N-(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (for example murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, for example, it has a mutagenized or deleted Fc receptor binding region.

The terms "fragment" or "antibody fragment" refer to a polypeptide derived from an antibody polypeptide molecule (for example, an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (for example, diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (for example, Alirocumab), anti IL-6 mAb (for example, Sarilumab), and anti IL-4 mAb (for example, Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

A number of implementations of the present disclosure have been described. Nevertheless, it will be understood that various modifications may be made without departing from the spirit and scope of the present disclosure. Accordingly, other implementations are within the scope of the following claims.

What is claimed is:

1. An electronics assembly for an injection device, comprising:
   one or more sensors configured to capture injection information of the injection device;
   one or more processors configured to be communicatively coupled to the one or more sensors; and
   a memory communicatively coupled to the one or more processors, the memory storing instructions which, when executed by the one or more processors, cause the one or more processors to perform operations comprising:
      receiving the injection information from the one or more sensors;
      determining, based on the injection information, a dwell time for a user of the injection device;
      receiving user information of the user, wherein determining the dwell time is further based on the user information of the user; and
      causing one or more display devices to provide feedback information to the user, the feedback information indicating the determined dwell time.

2. The electronics assembly of claim 1, wherein the injection information comprises at least one of: a speed of an injection, a dosage amount of an injection, or a profile of an injection.

3. The electronics assembly of claim 1, wherein causing the one or more display devices to provide feedback information comprises causing the one or more display devices to display an animation illustrating an injection process that comprises the determined dwell time.

4. The electronics assembly of claim 1, wherein the user information indicates one or more of: a weight of the user, a body fat percentage of the user, or a needle aversion of the user.

5. The electronics assembly of claim 1, wherein causing the one or more display devices to provide feedback information comprises transmitting the feedback information to a mobile device of the user which, when received by the mobile device, causes the mobile device to display one or more graphical representations representing injection instructions.

6. The electronics assembly of claim 1, the operations further comprising:
   determining, based on the captured injection information, a speed of injection of the user;
   comparing the speed of injection with an injection speed threshold; and
   responsive to determining that the speed of injection exceeds the injection speed threshold, activating an alert module.

7. The electronics assembly of claim 1, wherein the dwell time is further determined based on a drug type.

8. An injection device, comprising:
   a stopper comprising an electronics assembly, the electronics assembly comprising:
      one or more sensors configured to capture injection information of the injection device;
      one or more processors configured to be communicatively coupled to the one or more sensors; and
      a memory communicatively coupled to the one or more processors, the memory storing instructions which, when executed by the one or more processors, cause the one or more processors to perform operations comprising:
         receiving the injection information from the one or more sensors;
         determining, based on the injection information, a dwell time for a user of the injection device;
         receiving user information of the user, wherein determining the dwell time is further based on the user information of the user; and
         causing one or more display devices to provide feedback information to the user, the feedback information indicating the determined dwell time.

9. The injection device of claim 8, wherein the injection information comprises at least one of: a speed of an injection, a dosage amount of an injection, or a profile of an injection.

10. The injection device of claim 8, wherein causing the one or more display devices to provide feedback information comprises causing the one or more display devices to display an animation illustrating an injection process that comprises the determined dwell time.

11. The injection device of claim 8, wherein the user information indicates one or more of: a weight of the user, a body fat percentage of the user, or a needle aversion of the user.

12. The injection device of claim 8, wherein causing the one or more display devices to provide feedback information comprises transmitting the feedback information to a mobile device of the user which, when received by the mobile device, causes the mobile device to display one or more graphical representations representing injection instructions.

13. The injection device of claim 8, the operations further comprising:
   determining, based on the captured injection information, a speed of injection of the user;
   comparing the speed of injection with an injection speed threshold; and
   responsive to determining that the speed of injection exceeds the injection speed threshold, activating an alert module.

14. The injection device of claim 8, further comprising the one or more display devices.

15. The injection device of claim 8, wherein the dwell time is further determined based on a drug type.

16. A computer-implemented method, comprising:
   receiving injection information from one or more sensors of an injection device;
   determining, based on the injection information, a dwell time for a user of the injection device;
   receiving user information of the user, wherein determining a dwell time is further based on the user information of the user; and
   causing one or more display devices to provide feedback information to the user, the feedback information indicating the determined dwell time.

17. The method of claim 16, wherein the injection information comprises at least one of: a speed of an injection, a dosage amount of an injection, or a profile of an injection.

18. The method of claim 16, wherein causing the one or more display devices to provide feedback information comprises causing the one or more display devices to display an animation illustrating an injection process that comprises the determined dwell time.

19. The method of claim 16, wherein the user information indicates one or more of: a weight of the user, a body fat percentage of the user, or a needle aversion of the user.

20. The method of claim 16, wherein the dwell time is further determined based on a drug type.

* * * * *